(12) United States Patent
Lechmann et al.

(10) Patent No.: US 7,637,956 B2
(45) Date of Patent: Dec. 29, 2009

(54) ARTICULATED ENDOPROSTHESIS

(75) Inventors: Beat Lechmann, Bettlach (CH); Roger Bürki, Balsthal (CH); Dominique Burkard, Gretzenbach (CH); Robert Frigg, Bettlach (CH); Daniel Odermatt, Bettlach (CH)

(73) Assignee: Synthes USA, LLC, West Chester, PA (US)

( * ) Notice: Subject to any disclaimer, the term of this patent is extended or adjusted under 35 U.S.C. 154(b) by 601 days.

(21) Appl. No.: 11/338,466

(22) Filed: Jan. 23, 2006

(65) Prior Publication Data
US 2006/0212123 A1 Sep. 21, 2006

Related U.S. Application Data

(63) Continuation of application No. PCT/CH03/00494, filed on Jul. 22, 2003.

(51) Int. Cl.
A61F 2/44 (2006.01)
(52) U.S. Cl. .................................. 623/17.15
(58) Field of Classification Search .... 623/17.11–17.16
See application file for complete search history.

(56) References Cited

U.S. PATENT DOCUMENTS

| 3,658,056 | A | | 4/1972 | Huggler et al. | |
|---|---|---|---|---|---|
| 4,840,631 | A | | 6/1989 | Mathys | |
| 5,662,158 | A | | 9/1997 | Caldarise | |
| 5,879,407 | A | | 3/1999 | Waggener | |
| 5,893,889 | A | | 4/1999 | Harrington | |
| 5,895,428 | A | * | 4/1999 | Berry | 623/17.15 |
| 5,989,291 | A | * | 11/1999 | Ralph et al. | 623/17.15 |
| 6,517,580 | B1 | | 2/2003 | Ramadan et al. | |
| 6,770,095 | B2 | | 8/2004 | Grinberg et al. | |
| 6,918,934 | B2 | * | 7/2005 | Ralph et al. | 623/17.14 |
| 6,936,071 | B1 | | 8/2005 | Marnay et al. | |
| 7,214,243 | B2 | * | 5/2007 | Taylor | 623/17.11 |
| 7,258,699 | B2 | * | 8/2007 | Errico et al. | 623/17.14 |
| 2002/0035400 | A1 | * | 3/2002 | Bryan et al. | 623/17.15 |

FOREIGN PATENT DOCUMENTS

| DE | 100 37 504 | 2/2002 |
|---|---|---|
| DE | 101 30798 | 7/2003 |

OTHER PUBLICATIONS

International Search Report dated Mar. 2, 2004.
PCT International Preliminary Examination Report dated Nov. 7, 2005.

* cited by examiner

Primary Examiner—Anu Ramana
(74) Attorney, Agent, or Firm—Stroock & Stroock & Lavan LLP

(57) ABSTRACT

An endoprosthesis for a joint, in particular a an intervertebral implant with a central axis, a top part, a bottom part and a joint provided between them, wherein the joint comprises at least two articular surfaces A and B that can slide on one another; the top part has a top apposed surface that intersects the central axis and lateral surfaces; the bottom part has a bottom apposed surface that intersects the central axis and lateral surfaces; and wherein the endoprosthesis comprises at least one channel suitable to convey body fluid, said channel terminating in one of the two articular surfaces A and B and connecting it with the exterior of the endoprosthesis for the joint.

12 Claims, 5 Drawing Sheets

ARTICULATED ENDOPROSTHESIS

CROSS-REFERENCE TO RELATED APPLICATION

This application is a continuation of International Patent Publication PCT/CH2003/000494, filed Jul. 22, 2003, which is incorporated by reference herein in its entirety.

FIELD OF THE INVENTION

The present invention relates to an joint, in particular to an endoprosthesis and most particularly to an artificial intervertebral implant.

BACKGROUND OF THE INVENTION

Most intervertebral implants or intervertebral disk prosthesises used currently comprise a joint, the articular surfaces of which are made from metal, polymers or ceramic materials. The articular surfaces remain usually dry, due to which the service life of the implant may be impaired. In addition, due to the limited rotational movement of the parts of the joint, mounted superposed in a sliding manner, the tribological properties are of importance.

EP-B 0 193 538 to Marnay et al. discloses an artificial acetabulum that is fitted with a fluid chamber to improve the tribological properties of the articular surfaces. A disadvantage of this implant is that the fluid chamber is enclosed, so that no body fluid can be absorbed from outside the chamber. Furthermore, if body fluid does penetrate into the fluid chamber, for example through fissures from the outside, body fluid may accumulate in the enclosed fluid chambers. Due to lack of circulation the pH value of this accumulated fluid may drop, resulting in a possible chemical attack on parts of the implant. In addition, the enclosed fluid chambers, which are connected with the external surfaces of the implant through such fissures, may exhibit an undesirable pumping effect caused by the relative movements of the parts of the implant.

SUMMARY OF THE INVENTION

The object of the invention is to produce an endoprosthesis for a joint that comprises one or a plurality of channels terminating in the boundary surfaces between the implant and the bones, said channels being suitable to supply body fluids, containing proteins and other substances with good lubricating qualities, to articular surfaces mounted superposed in a sliding manner.

The intervertebral implant herein described includes a central axis, a top part, a bottom part and a joint part. The top part comprises a top surface that is substantially perpendicular to the central axis. The bottom part comprises a bottom surface that is substantially perpendicular to the central axis. The joint is provided axially between the top part and the bottom. The joint comprises a top and a bottom articular surface that slide on one another, wherein the top articular surface is connected to the top part and the bottom articular surface is connected to the bottom part. A lower channel suitable to convey body fluid, connects the top articular surface with the top surface. And an upper channel suitable to convey body fluid, connects the bottom articular surface with the bottom surface.

In another embodiment the implant has a plurality of upper channels or a plurality of lower channels.

In a further embodiment, at least one of the lower or upper channels are so arranged that their longitudinal axes form an angle between 0° and 90° with the central axis.

In another embodiment, the channels have a cross-section that is between 0.01% and 10% of the articular surface it terminates in.

In a further embodiment the channels have a diameter between 0.3 mm and 4.0 mm.

In another embodiment the channels are symmetrically distributed in the articular surfaces.

In further embodiment the articular surfaces of the joint parts are produced from material pairs of metal/polymer, metal/metal or ceramics/ceramics.

In another embodiment at least one channel is substantially rounded at the point of termination in the top or bottom articular surface.

In a further embodiment the joint comprises a top joint part with a top articular surface, a central joint part with a first central articular surface and a second central articular surface, and a bottom joint part with a bottom articular surface. The top articular surface has a convex shape and the first central articular surface has a matching surface so that the top articular surface and the first central articular surface slide on one another. The bottom articular surface has a convex shape and the second central articular part has a matching surface so that the bottom articular surface and the second central articular surface slide on one another. At least one upper channel suitable to convey body fluid, said channel terminating in the top articular surface and connecting it with the first articular surface. At least one lower channel suitable to convey body fluid, said channel terminating in the bottom articular surface and connecting it with the second articular surface. There may be a plurality of lower or upper channels. The axis of rotation of the top joint part relative to the central joint part may be substantially perpendicular to the axis of rotation of the central joint part relative to the bottom joint part.

Thus the present invention allows the provision of one or a plurality of channels terminating in the boundary surfaces between the implant and the bones, said channels being suitable to supply body fluids, containing proteins and other substances with good lubricating qualities, to the articular surfaces mounted superposed in a sliding manner.

BRIEF DESCRIPTION OF THE DRAWINGS

The features of the invention will be better understood by reference to the accompanying drawings which illustrate presently preferred embodiments of the invention. It will nevertheless be understood that the invention should not be limited to such preferred embodiments and that the features may be used singularly or in combinations and that modification and alterations of the illustrated and described devices and methods are contemplated. In the drawings:

FIG. 1b is a detail of the bottom joint part of the embodiment of the intervertebral implant illustrated in FIG. 1a.

DETAILED DESCRIPTION OF THE INVENTION

Figure 1A:
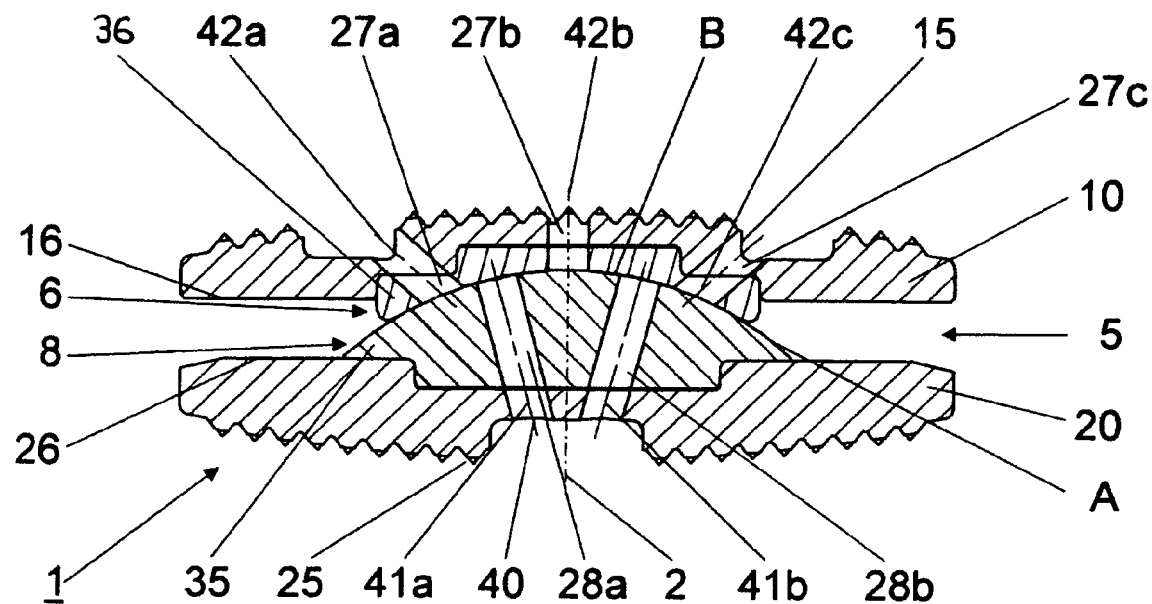
FIG. 1a is a mediolateral section through an embodiment of intervertebral implant.

In FIG. 1 a medio-laterally sectioned embodiment of the endoprosthesis for a joint for an intervertebral implant 1 is illustrated. The intervertebral implant 1 illustrated in FIG. 1 comprises a top part 10 and a bottom part 20, which enclose a joint 5 and are axially superimposed relative to central axis 2 that is substantially parallel to the longitudinal axis of the spine. The top part 10 has a top apposed surface 15 for the purpose of placing it adjacent a vertebra located above The top apposed surface 15 axially protrudes and is substantially perpendicular to the central axis 2. The top part 10 also has a bottom inside surface 16 preferably with an integrated top joint part 6.

Analogously to that, the bottom part 20 has a bottom apposed surface 25 for the purpose of placing it adjacent a vertebra located below. The bottom apposed surface 25 axially protrudes and intersects the central axis 2. The bottom part 20 also has an inside top surface 26 preferably with the integrated bottom joint part 8. The bottom joint part 8 is configured as a spherical segment 35 with a first articular surface A. The top joint part 6 is preferably constructed as a joint shell 36 corresponding to the spherical segment 35 and with a second articular surface B, so that the top and bottom part 10, 20 can pivot polyaxially relative to one another by means of the joint 5. The two joint parts 6, 8 are preferably constructed as separate parts and are joined with the corresponding top part 10 and bottom part 20.

On the top part 10, upper channels 27 may be provided which terminate in the top apposed surface 15 at upper openings 42 and pass through the top part 10 as well as the top joint part 6 down to the articular surface B of the joint shell 36. Body fluid, having lubricating properties, preferably pass through these upper channels 27 from above to the articular surfaces A, B of the joint 5. Similarly, on the bottom part 20 lower channels 28 may be provided, which terminate in the bottom apposed surface 25 forming lower openings 41 and pass through the bottom part 20 as well as the bottom joint part 8 up to the articular surface A of the spherical segment 35, so that the body fluid may pass from below to the articular surfaces A, B of the joint 5. The channels 27, 28 preferably are so arranged in both the top and bottom part 10, 20, that their openings 42, 41 are situated centrally in the apposed surfaces 15, 25. In the embodiment of the intervertebral implant 1 illustrated in FIG. 1a the top joint part 6 is constructed with three upper channels 27a-c. The longitudinal axis 42b of the central upper channel 27b is approximately coaxial with the longitudinal axis 2. The longitudinal axes 42a, 42c of the two lateral upper channels 27a, 27c form an angle with the central axis 2, whereby the longitudinal axis 42a of the channel 27a forms an angle of about −50° with the central axis 2 and the longitudinal axis 42c of the channel 27c forms an angle of about +50° with the central axis 2. The bottom joint part 8 preferably comprises two lower channels 28a, 28b, the longitudinal axes 41a, 42b of which also include an angle with the central axis, whereby the longitudinal axis 41a of the channel 28a forms an angle of about −15° with the central axis 2 and the longitudinal axis 41b of the channel 28b forms an angle of about +15° with the central axis 2.

It will be noted that in this embodiment the upper and lower channels 27, 28 are so arranged, that at least one upper channel 27 terminates in the top apposed surface 15 and at least one lower channel 28 terminates in the bottom apposed surface 16, so that body fluid can be conveyed to both sides of the articular surfaces A, B.

Figure 1B:
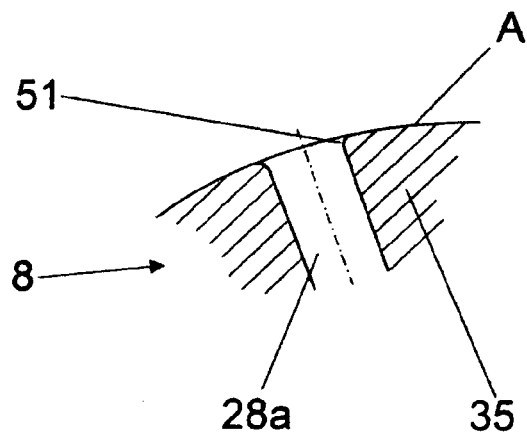

FIG. 1b illustrates a detail of the bottom joint part 8 with a lower channel 28a. The lower channel 28a passes through the spherical segment 35 up to the articular surface A, while at the transition the channel wall has a rounding or radius 51, so that the termination of the channel 28a into the articular surface A does not have a sharp edge but is rounded. The terminations of the other lower channel 28b, as well as of all upper channels 27a, 27b and 27c have preferably similar constructions. The advantage of rounding the terminations of the channels 27, 28 is that the articular surfaces A, B will not be damaged, as may be caused by transitions with sharp edges.

In FIGS. 2-5 a further embodiment of an endoprosthesis for a joint, constructed as an intervertebral implant 1, is illustrated. The intervertebral implant 1 comprises a top part 10, a bottom part 20 and a joint 5. The top part comprises a top apposed surface 15 preferably perpendicular to the central axis 2. The top surface is adapted to be adjacent to a vertebra. The bottom part 20 comprises a bottom apposed surface 25 preferably perpendicular to the central axis 2. The bottom part is adapted to be adjacent to a vertebra. The joint 5 lies on the central axis 2, joining top part 10 and bottom part 20, in a displaced manner relative one another about two axes 3,4 of rotation, situated at right angles to one another.

The joint 5 has a top joint part 6, a central joint part 7 and a bottom joint part 8. The top joint part 6 and central joint part 7 form a top rotary joint 38 that can rotate about a first axis of rotation 4. The top rotary joint 38 comprises a top convex articular surface 32 provided on the top joint part 6 and coaxial with the first axis 4 of rotation and a top concave articular surface 33, provided on the central joint part 7 and matching the articular surface 32.

The bottom joint part 8 and central joint part 7 form a bottom rotary joint 39 that can rotate about a second axis of rotation 3 that is perpendicular to the first axis of rotation 4. The bottom rotary joint 39 comprises a bottom convex articular surface 30, provided on the central joint part 7 and coaxial with the first axis 3 of rotation and a bottom concave articular surface 31, provided on the bottom joint part 8 and matching the articular surface 30.

The articular surfaces 30, 31, 32, 33 are constructed as partial jacket surfaces of cylinders with axially adjacent generated tapered surfaces at the end.

Furthermore, pins 17, coaxial with the axes 3, 4 of rotation, are fitted at the ends of the top and central joint part 6, 7. The pins 17 are displaceably accommodated in slotted guides 18 in the bottom joint part 8 and in the central joint part 7. By virtue of the pins 17, guided in the slotted guides 18, the rotation angles of the joint parts 6, 7, 8 about the axes 3, 4 of rotation are limited. In addition, the intervertebral implant 1 is held together by the pins 17 accommodated in the slotted guides 18.

Figure 2:
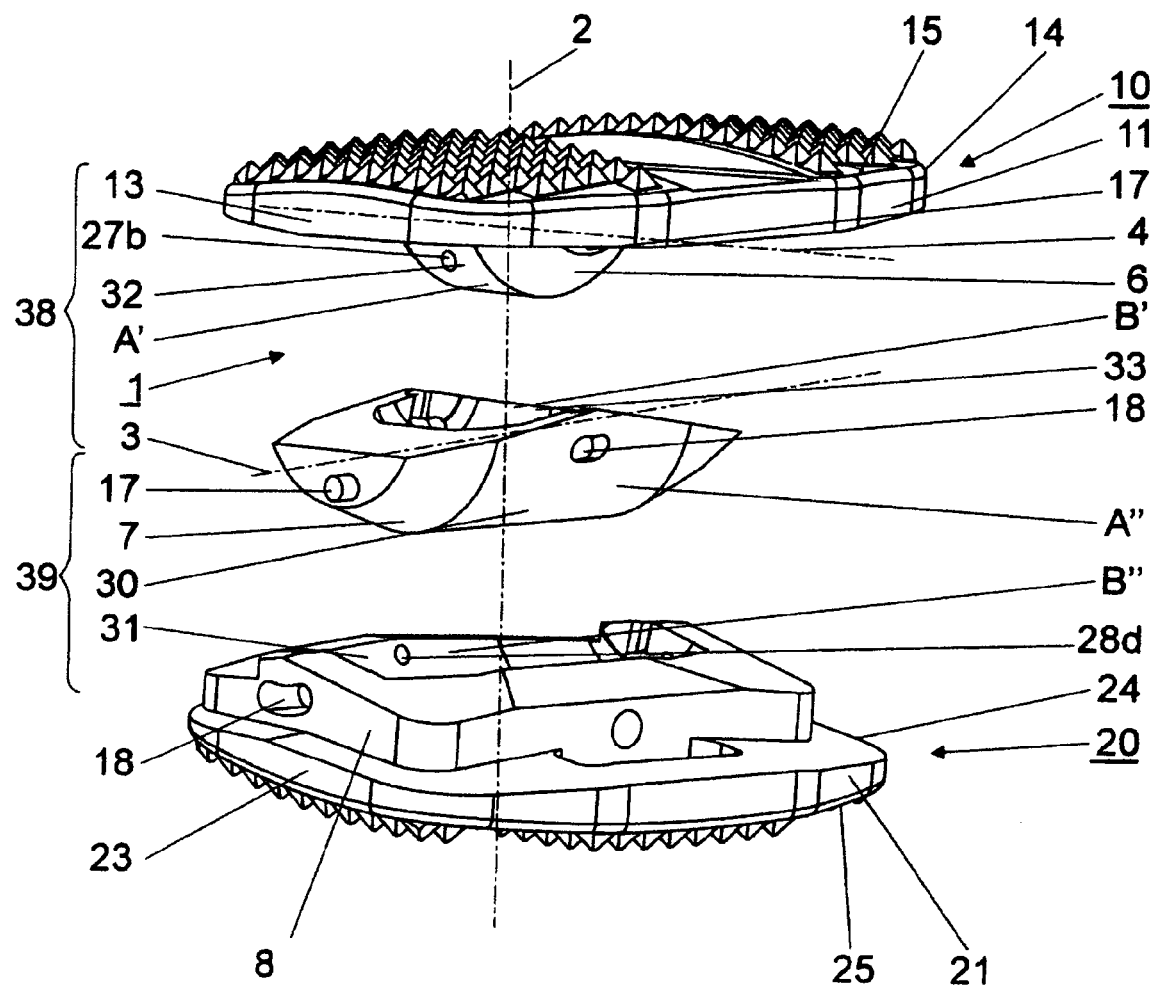
FIG. 2 is a perspective view of a further embodiment of an intervertebral implant according to the invention.
Figure 3:
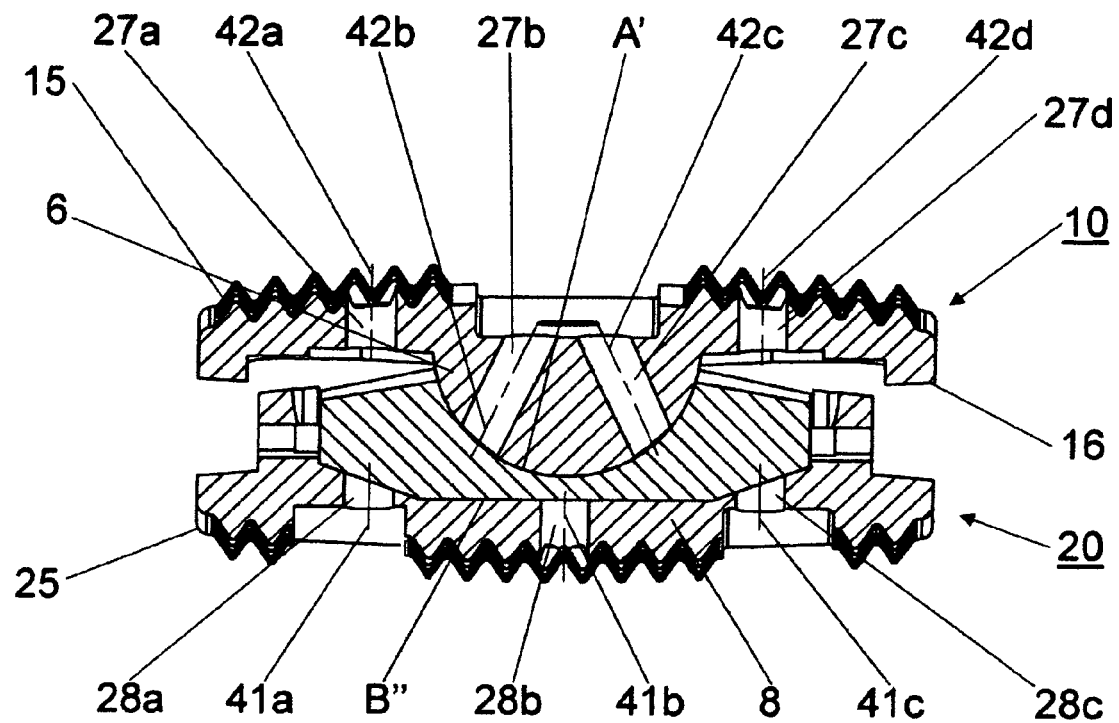
FIG. 3 is a section parallel to the first axis of rotation through the embodiment illustrated in FIG. 2.
Figure 4:
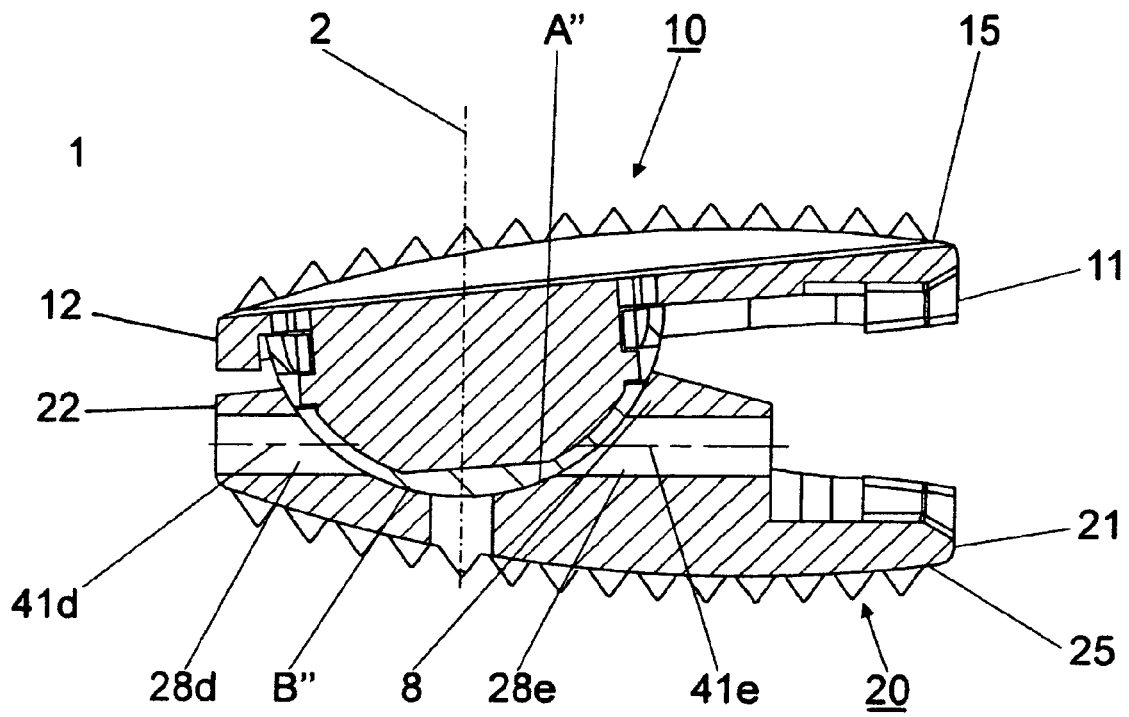
FIG. 4 is a section parallel to the second axis of rotation through the embodiment illustrated in FIGS. 2 and 3.

As it is shown in FIGS. 3 and 4, four upper channels 27a-d are provided in the top part 10, terminating in the top apposed surface 15, and pass through the top part 10, including the top joint part 6 up to the top articular surface A'. The body fluid, having the lubricating properties, is conveyed through these channels 27 from above to the articular surfaces A', B' of the top rotary joint 38 (FIG. 2). On the bottom part 20 three lower channels 28a-c are provided, which terminate in the bottom apposed surface 25 and pass through the bottom part 20, including the bottom joint part 8 up to the articular surface B", so that the body fluid can be conveyed from below to the articular surfaces A", B" of the bottom joint part 39 (FIG. 2). Furthermore, on the bottom joint part 8 two further channels 28d, 28e are provided (FIG. 4), which enter from the outside from the ventral and dorsal lateral surfaces 21, 22 into the bottom joint part 8 and pass through the bottom part 20, including the bottom joint part 8 up to the articular surfaces A", B". As it can be seen from the FIG. 3, only two of the four upper channels 27b, 27c terminate in the articular surface A' of the top joint part 6. The other two upper channels 27a, 27d terminate in the bottom surface 16 of the top part 10 and have longitudinal axes 42a, 42d, which are aligned parallel with the central axis 2. The longitudinal axes 42b, 42c of the two upper channels 27b, 27c include an angle with the central axis 2, while the longitudinal axis 42b of the upper channel 27b includes an angle of about +25° with the central axis 2 and the longitudinal axis 42c of the channel 27c includes an angle of about −25° with the central axis 2. Furthermore, it can be seen from FIG. 4, that the two lower channels 28d, 28e have longitudinal axes 41d, 41e, which are perpendicular to the central axis 2, while the longitudinal axis 41d of the lower channel 28d includes an angle of about +90° with the central axis 2, whereas the longitudinal axis 41e of the lower channel 28e includes an angle of about −90° with the central axis 2. Both longitudinal axes 41d, 41e are situated in the antero-posterior central plane of the intervertebral implant 1.

Figure 5:
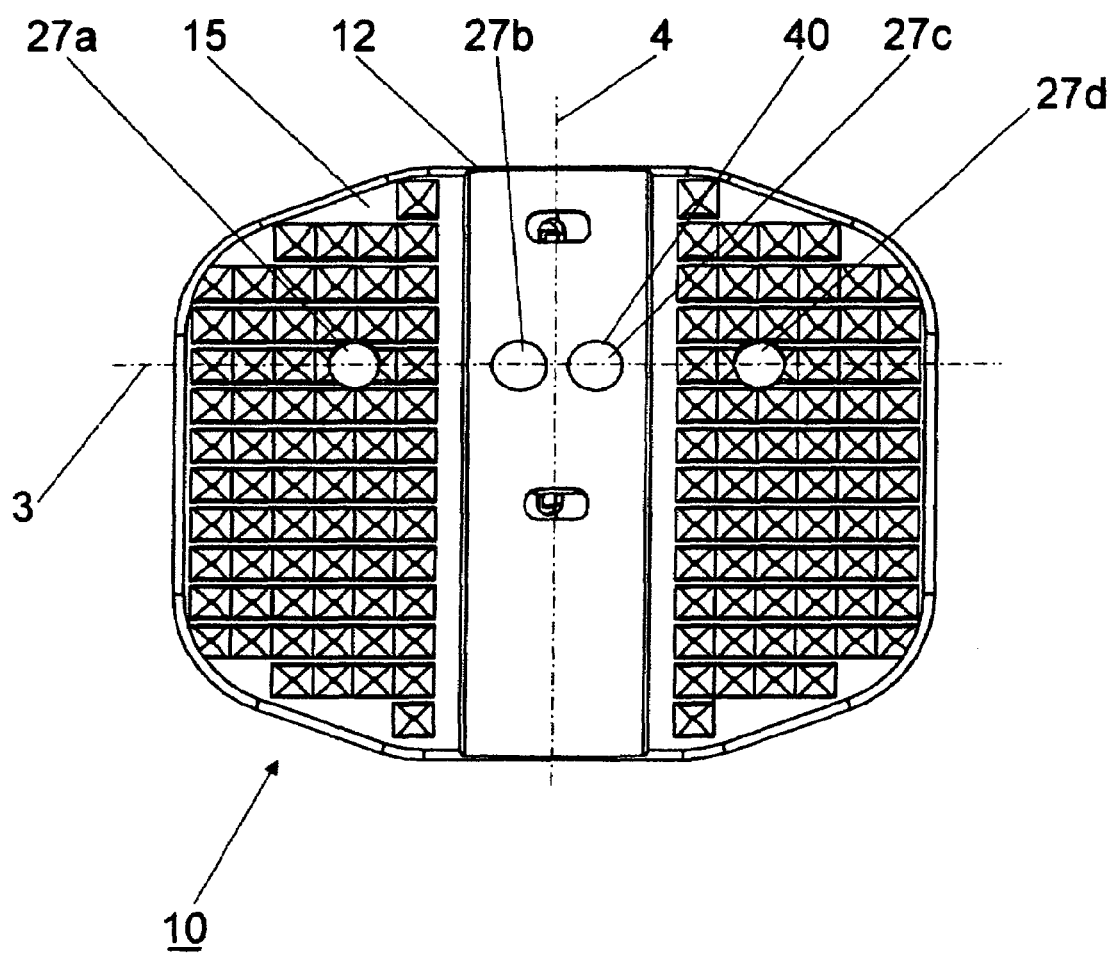
FIG. 5 is a top view on the embodiment illustrated in FIGS. 2 to 4.

FIG. 5 shows the openings 40 of the upper channels 27a-d terminating in the top apposed surface 15. The openings 40 are situated in a part surface of the apposed surface 15, that is preferably at right angles to the central axis 2 and is preferably concentric with it. The central axis 2 (FIG. 2) intersects the point of intersection of the first axis 3 of rotation with the second axis 4 of rotation and is displaced relative to the dorsal lateral surface 12 of the top part 10 from its centre.

The joint 5 can contain two or three joint parts in various embodiments made by pairs of materials such as metal/polymer, metal/metal, and ceramic/ceramic. Exemplary metals for such a joint 5 include alloys of cobalt, chromium and molybdenum. In the case of pairing metal with metal, the alloy can be enriched also with carbon. Likewise, the surface of a joint part, made from metal, can be coated with titanium carbide, titanium nitride or amorphous carbon, by using a suitable process. An exemplary polymer is a high-molecular polyethylene (UHMWPE), wherein the surface can be cross-linked by a suitable process to improving the wearing properties of the material.

In yet another embodiment the intervertebral implant comprises a plurality of upper channels 27 and preferably also a plurality of lower channels 28, which are so arranged, that their longitudinal axes include an angle between about 0° and about 90° with the central axis 2 of the intervertebral implant 1. The angle is chosen so that the strength of the intervertebral implant 1 remains adequate, the channels terminate in the articular surfaces A, B at the required positions, and the channels terminate on the outside of the intervertebral implant 1 where synovial fluid is available, in particular centrally on the apposed surfaces 15, 25 and at the cavity produced by the incision.

In a further embodiment each channel has a cross-section that is between about 0.01% and about 10% of one of the articular surfaces A, B. Suitable dimensions for the articular surface A' are between about 400 mm$^2$ and about 500 mm$^2$ and suitable dimensions for the articular surface A" are between about 200 mm$^2$ and about 300 mm$^2$. A suitable minimum cross-section for a channel is about 0.07 mm$^2$ and a maximum is about 12.6 mm$^2$. Suitable surface area for the top and bottom apposed surfaces 15, 25 are preferably about 900 mm$^2$ to about 1000 mm$^2$.

The channels 27, 28 have preferably a diameter between about 0.3 mm and about 4.0 mm. The minimum diameter is determined based upon the size of the particles which the channel is desired to transport, for example proteins. The maximum diameter of the channels 27, 28 is chosen so as not to cause significant weakening of the strength of the intervertebral implant 1.

In yet another embodiment, the channels terminate symmetrically in the articular surfaces A, B.

In another embodiment, the top apposed surface 15 has a surface area $F_o$, while the upper channels terminate in the top apposed surface 15 within a part surface having a surface area $T_o < F_o$. The surface area $T_o$ of the part surface is preferably between about 0.006% and about 1.0% of the surface area $F_o$ of the top apposed surface 15. Similarly, the bottom apposed surface has a surface area $F_u$, while the lower channels terminate in the bottom apposed surface within a part surface with a surface area $T_u < F_u$, while the surface area $T_u$ of the part surface is preferably between about 0.006% and about 1.0% of the surface area $F_u$ of the bottom apposed surface. Furthermore, these part surfaces are arranged preferably concentrically with the central axis of the intervertebral implant.

In another embodiment at least one upper and lower channel 27, 28 enters into the corresponding part of the joint 5 from a lateral surfaces of the top part 10 or the bottom part 20. This allows that body fluid to be conveyed to the articular surfaces from the cavity, produced by the an incision during implantation of the implant.

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being indicated by the appended claims, and not limited to the foregoing description.

What is claimed:

1. An intervertebral implant comprising:
    a central axis;
    a top part comprising a top apposed surface intersecting the central axis, a bottom inside surface, and at least one upper channel extending from the top apposed surface to the bottom inside surface;
    a bottom part comprising a bottom apposed surface intersecting the central axis, a top inside surface, and at least one lower channel extending from the bottom apposed surface to the top inside surface;
    a top joint part located between the top and bottom parts, the top joint part defining a first end surface, in contact with the bottom inside surface of the top part, a first curved articulating surface opposite the first end surface, and at least one upper joint channel extending from the first end surface to the first curved articulating surface and in communication with at least one upper channel to convey fluid to the first curved articulating surface;
    a bottom joint part located between the top and bottom parts, the bottom joint part defining a second end surface, in contact with the top inside surface of the bottom part, a second curved articulating surface opposite the second end surface, the second curved articulating surface contacting the first curved articulating surface of the top joint part, and at least one lower joint channel extending from the second end surface to the second curved articulating surface and in communication with at least one lower channel to convey fluid to the second curved articulating surface.

2. An implant according to claim 1, wherein the implant has a plurality of non-coaxial upper channels extending from the top apposed surface to the bottom inside surface, and a plurality of non-coaxial upper joint channels extending from the first end to the first curved articulating surface.

3. An implant according to claim 1, wherein the implant has a plurality of non-coaxial lower channels extending from the bottom apposed surface to the top inside surface, and a plurality of non-coaxial lower joint channels extending from the second end to the second curved articulating surface.

4. An implant according to claim 1, wherein the at least one lower channel, the at least one lower joint channel, the at least one upper channel, and the at least one upper joint channel each include a longitudinal axis, each of the longitudinal axes forming an angle between about 0° and about 90° with the central axis.

5. An implant according to claim 1, wherein the at least one lower channel and the at least one upper channel have a cross-sectional area that is between about 0.01% and about 10% of the articular surface they intersect.

6. An implant according to claim 1, wherein the at least one upper channel and the at least one lower channel each have a diameter between about 0.3 mm and about 4.0 mm.

7. An intervertebral implant comprising:
   a central axis;
   a top part comprising a top apposed surface intersecting the central axis, a bottom articulating surface being at least a partially curved surface, and at least one upper channel extending from the top apposed surface to the bottom articulating surface;
   a bottom part comprising a bottom apposed surface intersecting the central axis, a top articulating surface the top articulating surface being curved, and at least one lower channel extending from the bottom apposed surface to the top articulating surface;
   a joint part located between the top part and the bottom part, the joint part including a first articulating surface having at least a partially curved surface configured to directly contact the bottom articulating surface of the top part, and a second articulating surface opposite the first articulating surface configured to directly contact the top articulating surface of the bottom part; and
   wherein the at least one upper channel conveys fluid from the top apposed surface to the first articulating surface and the at least one lower channel conveys fluid from the bottom apposed surface to the second articulating surface wherein the implant has a plurality of non-coaxial upper channels extending from the top apposed surface to the bottom articulating surface of the top part.

8. An implant according to claim 7, wherein the implant has a plurality of non-coaxial lower channels extending from the bottom apposed surface to the top articulating surface of the bottom part.

9. An implant according to claim 7, wherein the at least one lower channel and the at least one upper channel each include a longitudinal axis, each of the longitudinal axes forming an angle between about 0° and about 90° with the central axis.

10. An implant according to claim 7, wherein each of the at least one lower channel and the at least one upper channel each have a cross-sectional area that is between about 0.01% and about 10% of the articular surface they terminate in.

11. An implant according to claim 7, wherein each of the at least one upper channel and the at least one lower channel has a diameter between about 0.3 mm and about 4.0 mm.

12. An implant according to claim 7, wherein there are a plurality of lower channels symmetrically distributed in the bottom part and a plurality of upper channels symmetrically distributed in the top part.

* * * * *